US006699282B1

(12) United States Patent  
Sceusa

(10) Patent No.: US 6,699,282 B1
(45) Date of Patent: Mar. 2, 2004

(54) METHOD AND APPARATUS FOR DELIVERY OF MEDICATION

(75) Inventor: Nicholas A. Sceusa, New York, NY (US)

(73) Assignee: Gelsus Research and Consulting, Inc., New York, NY (US)

( * ) Notice: Subject to any disclaimer, the term of this patent is extended or adjusted under 35 U.S.C. 154(b) by 0 days.

(21) Appl. No.: 10/379,682

(22) Filed: Mar. 6, 2003

(51) Int. Cl.[7] ................................................. A61F 2/06
(52) U.S. Cl. ...................... 623/1.42; 128/898; 604/501; 604/20; 424/425; 623/921
(58) Field of Search ............................... 623/1.42, 1.43, 623/1.46, 921; 424/424, 425; 606/34; 607/115; 427/2.25; 604/501, 20

(56) References Cited

U.S. PATENT DOCUMENTS

| 4,585,652 A | * | 4/1986 | Miller et al. ............. 604/891.1 |
| 5,545,213 A | * | 8/1996 | Keogh et al. ................. 600/36 |
| 5,588,962 A | * | 12/1996 | Nicholas et al. ............ 604/507 |
| 5,843,172 A | | 12/1998 | Yan |
| 6,219,577 B1 | * | 4/2001 | Brown et al. ................. 604/20 |
| 6,317,615 B1 | | 11/2001 | KenKnight et al. |
| 2002/0098278 A1 | | 7/2002 | Bates et al. |
| 2002/0183830 A1 | | 12/2002 | Su et al. |

* cited by examiner

Primary Examiner—Corrine McDermott
Assistant Examiner—Thomas J Sweet
(74) Attorney, Agent, or Firm—Browdy and Neimark, P.L.L.C.

(57) ABSTRACT

An implanted device such as a stent is provided which is capable of holding an induced charge or sufficient magnitude that the device may, by electrostatic means, attract the bioactive material to itself. The charge, either positive or negative, or relative to the bioactive material sufficiently positive or negative, is deposited into the implantable device via an exterior induction coil. The implantable device itself becomes an introduced "dosage form", becoming part of a biologically closed electric circuit, through which the bioactive material is attracted to the implanted device.

14 Claims, 2 Drawing Sheets

METHOD AND APPARATUS FOR DELIVERY OF MEDICATION

FIELD OF THE INVENTION

The present invention is directed to a method and apparatus for delivering medication over a prolonged period. The method included charging or recharging an implanted device which has been or can be impregnated with a bioactive ingredient without the requirement for removing the device from the body.

BACKGROUND OF THE INVENTION

It has become common to treat a variety of medical conditions by temporarily or permanently introducing an implantable medical device partly or completely into the esophagus, trachea, colon, biliary tract, urinary tract, vascular system, or other locations within a human or veterinary patients. Many treatments of the vascular or other systems entail introducing a device such as a stent, a catheter, a balloon, a wire guide, a cannula, or the like.

Some drawbacks can be encountered during use of a stent or other implantable medical device. For example, when a device is introduced into and manipulated through the vascular system of a patient, the blood vessel walls can be disturbed or injured. Clot formation or thrombosis often results at the injured site, causing stenosis (closure) of the blood vessel. Moreover, if the medical device is left within the patient for an extended period of time, thrombus often forms on the device itself, again causing stenosis. As a result, the patient is placed at risk of a variety of complications, including heart attack, pulmonary embolism, and stroke. Thus, the use of such a medical device can entail the risk of precisely the problems that its use was intended to ameliorate.

The efficacy of a stent can be assessed by evaluating a number of factors, such as thrombosis, neotimimal hyperplasia, smooth muscle cell migration and proliferation following implantation of the stent, injury to the artery wall, overall loss of luminal patency, stent diameter in vivo, thickness of the stent, and leukocyte adhesion to the luminal lining of tented arteries. However, the chief areas of concern are early subacute thrombosis and eventual restenosis of the blood vessel due to intimal hyperplasia.

Other conditions and diseases are treatable with stents, catheters, cannulae, and other medical devices inserted into the esophagus, trachea, colon, biliary tract, urinary tract, and other locations in the body. A wide variety of bioactive materials, including drugs, therapeutic agents, diagnostic agents, and other materials having biological or pharmacological activity within a patient, have been applied to such medical devices for the purpose of introducing such materials into the patient. Unfortunately, the durable application of bioactive materials to these medical devices and the like, sufficient for such introduction to occur, is often problematic. A range of impregnated or layered materials have been applied to such devices to permit the timed release of bioactive materials from such devices, or even to permit bioactive materials to be applied to such devices at all. Therapeutic pharmacological agents have been developed to improve successful placement of the medical device as well as to be delivered to the site of device implantation. Among the drugs that can be delivered via impregnated or loaded medical devices are those that can treat restenosis, tissue inflammation, promote endotheliazation or any other disease that may inhibit the successful implantation and retention of the device.

Implantable devices made of biologically acceptable metals were previously unable to deliver localized bioactive materials to tissues at the location treated by the device. However, there are polymeric materials that can be loaded with and release bioactive materials, including drugs or other pharmacological treatment, which can be used for drug delivery.

Yan, in U.S. Pat. No. 5,843,172, the entire contents of which are hereby incorporated by reference, describes a stent made of metal which has porous cavities in the metallic portion of the stent so that the drugs can be loaded directly into the pores without substantially weakening the structural and mechanical characteristics of the prosthesis. However, once the bioactive material has been depleted from the stent, if it is still necessary to deliver the material to the site of the stent, the stent must be replaced.

SUMMARY OF THE INVENTION

It is an object of the present invention to overcome the aforesaid deficiencies in the prior art.

It is another object of the present invention to provide an implantable device which can be recharged with a bioactive material.

It is a further object of the present invention to provide an implantable device which can be charged with a bioactive material.

According to the present invention, an implantable device such as a stent is provided which is capable of holding an induced charge of sufficient magnitude that the device may, by electrostatic means, attract bioactive material to itself. The charge, either positive or negative, or relative to the bioactive material sufficiently positive or negative, is deposited into the implantable device via an exterior induction coil. The implantable device itself becomes an introduced "dosage form", becoming part of a biologically closed electric circuit, as shown in Nordenstrom, B. E., Biologically Closed Electrical Systems; Stockholm, Nordic Medical Publications, 1983. This mechanism is similar to that described in Sceusa, U.S. Pat. No. 6,414,033, the entire contents of which are hereby incorporated by reference.

The bioactive ingredient, which may be in ionic form as described in Sceusa, supra, or in a neutral complex that will dissociate tonically in the presence of the charge of the implantable device, will then attach itself to the implantable device.

The implantable device must possess the correct electronic transfer system to permit an induced charge to form, to be carried, and to be retained long enough to act electrostatically and attract the medication to itself. Many materials having these properties are known, including plastics and ceramics which have metal atoms covalently bonded into the matrix, or an entirely ceramic material without metal ions, having the correct electronic transfer system. Alternatively, the implantable device can be made with a metallic or capacitive strip entirely embedded within the device to drive the accretion of medication into the matrix of the device. In yet another embodiment, the implantable device can be made of porous metal, such as disclosed in Yan, U.S. Pat. No. 5,843,172. Any conventional physiologically acceptable material which has the needed electron transfer (capacitance) systems can be used in the present invention.

To recharge or charge the implantable device, the bioactive material can be delivered intravenously or transmembrane by one of two systems:

1. Intravenous injection, which is minimally invasive; or

2. Teorell-Meyer dosage or "reverse" Teorell-Meyer forms, depending upon the anatomy and location of the implantable medical device.

The bioactive material should be in a "reverse" Teorell-Meyer dosage form as follows:

1. It may be a neutral complex of the bioactive ingredient and a suitable carrier molecule, or a synthetic carrier molecule, such that the $K_d$ (the constant of dissociation), which is the reciprocal of the $K_a$ (constant of association), is less than the electrostatic force of attraction exerted by the implantable device for the bioactive material. Thus, the medication will leave the carrier molecule and become embedded in the implantable device.
2. The bioactive ingredient may be a stable charged complex with a direct attraction for the charge in the implantable device.

DETAILED DESCRIPTION OF THE INVENTION

Figure 1:
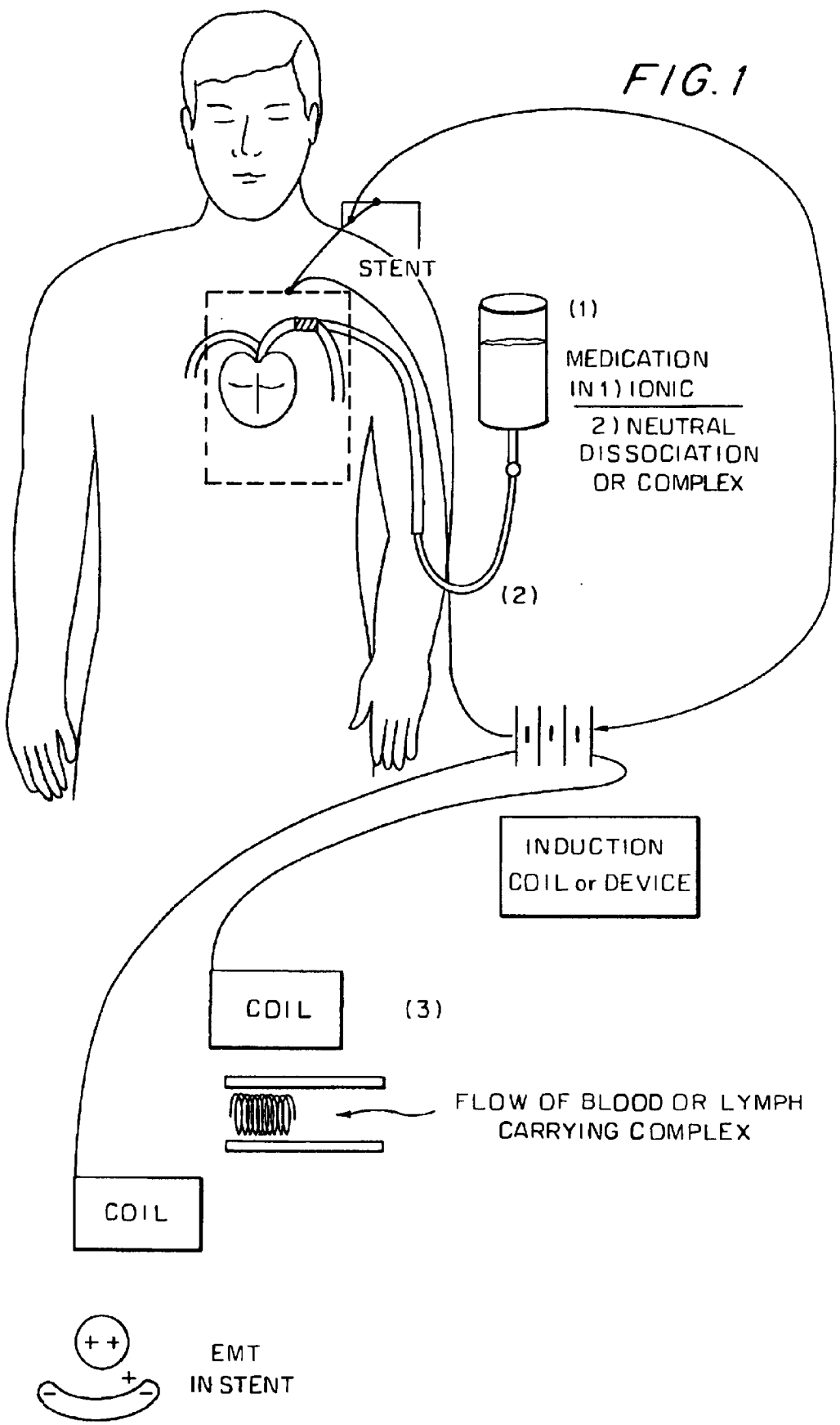
FIG. 1 illustrates a method for charging or recharging an implantable device in vivo.

The present invention provides a method for charging or recharging an implanted device with a bioactive material. FIG. 1 illustrates the present invention using a stent as the implanted device. Bioactive material 1, in ionic or neutral-dissociated complex, is introduced, in this case, intravenously. An induction coil or device 2 ensures that the implanted device is appropriately electrostatically charged. The difference in charge between the implanted device and the bioactive agent causes the bioactive agent to be attracted to the implanted device.

All cells acquire the molecules and ions they need from the surrounding milieu, usually the extracellular fluid. There is an unceasing traffic of molecules and ions ion and out of the cell through the cell's plasma membrane. The cell membrane is a lipid bilayer that functions as a selective barrier for entry and exit of substances, i.e., the membrane is semipermeable. The membrane is permeable to water molecules and a few other small, uncharged molecules such as oxygen and carbon dioxide. These molecules freely diffuse in and out of the cell. However, it is not permeable to ions, small hydrophilic molecules that are attracted to water and other polar solvents, such as glucose, and macromolecules such as proteins. Good lipid solubility is an important factor in the assessment of absorption. Unionized or neutral species are more lipid-soluble, and hence are more readily absorbed.

Simple diffusion is the most basic type of transport in the cell. Diffusion moves atoms, ions and molecules from a region of higher concentration to a region of lower concentration. This difference between regions is referred to as a concentration gradient. If differing concentrations of molecules, in two regions, are separated by a permeable membrane, the molecules will diffuse through the membrane from a higher to a lower concentration, until they reach an equal concentration on both sides. Without permeability, diffusion will not occur even if a difference in concentration exists. Osmosis is the diffusion of water through the membrane to equalize the concentrations on either side of the membrane. In osmosis, water must move because the dissolved particles are too large to pass through the membrane. The rate of diffusion of a particle across a membrane will vary depending on the size, polarity, charge, and concentration of the molecule on the inside of the membrane versus the concentration on the outside of the membrane.

The Teorell-Meyer™ dosage forms depend upon bioelectricity for their function. Two researchers were active in this field prior to the discovery of these dosage forms: the Biologically Closed Electric Circuit (BCEC) of Dr. Bjorn Nordenstrom, and the pioneering work on electro-osmotic phenomena in general biology and membranes of Dr. Torsten Teorell and Dr. Karl Meyer. U.S. Pat. No. 6,414,033, is directed to dosage forms based upon the Teorell-Meyer gradient equations.

A biologically closed electric circuit is physiologically analogous to an ordinary electric circuit, except that predominantly ions, as well as electrons, move along and through it. In biological material, the co-transport of electrons occurs in short redox steps. Ions are transported electro-osmotically. Concentration, and consequently, electrical gradients, are maintained by Donnan Equilibria, which are large sheets of charge in the tissue proteins, and by ion pumps functioning at the expense of ATP. The second half of the circuit, the return halve, takes place via passive or facilitated diffusion. Ions will follow, or will respond to the flow of current according to their net charge, from one area of chare density to another area of different charge density, as part of the usual BCEC circulation. The local viscosity and the electrical path length, which is a vector quantity, play an important role. Vectors have the properties of force, distance (length), according to the gradients that comprise these vectors. Controlling the electrical vector makes it possible to control the path of the ion, because the electrical vector is very many times stronger than any of the other forces which act on an ion.

It is important to remember that a BCEC may be electrically closed but thermodynamically and physiologically open, so that a dosage form may be placed therein. The present invention takes advantage of this property to induce a gradient artificially, using appropriate buffering, companion, and carrier molecules. Certain molecules may act as all three at the same time, and the amino acids and their congeners have been found to be ideal for this purpose. By introducing the dosage form which has been specifically designed and buffered for a particular compartment, the pH of the recipient compartment, in which the form is placed, is changed relative to the target compartment, thus setting up an induced gradient and a corresponding concentration cell. This is provided for by the Lewis acid-base definitions, which makes it possible to consider all positive charges as a acids and all negative charges as bases.

Inducing the pH changes and thus taking control of the bio-electrical field and corresponding electrical vector makes it possible to manipulate the direction of ionic flow and transport. Since the electrical vector is many times more powerful than the other vectors acting in the system, it is possible to stop or reverse the ionic flow for the time that the induced field is present. If the electrical vector is coupled to act in the same direction as other vectors in the system, the effect is most powerful. The three vectors which are known to act in physiological systems are the hydrostatic vector, the particulate (colligative) vector, and the electro-motive force (electro-osmotic) vector.

It should also be taken into account that the association constant ($K_a$) and its reciprocal, the dissociation constant ($K_c$), for any complex is pH dependent. In the context of an electrical gradient inside a concentration cell, it may also be considered electrically dependent. In other words, at one pH a complex may be completely associated, and at another pH, may be almost completely dissociated.

For any given complex, a concentration cell has a continually changing spectrum of pH and association constants inherent within it. This change over distance, which operates primarily, or most strongly, at the endpoints, is what allows the system to receive and deliver bioactive materials in the way it does. By carefully choosing complexes and mixed ligand complexes, with different $K_a$, it is possible to deliver a bioactive material directly to the location of the implanted device so that the device is charged or recharged with the bioactive material.

Figure 2:
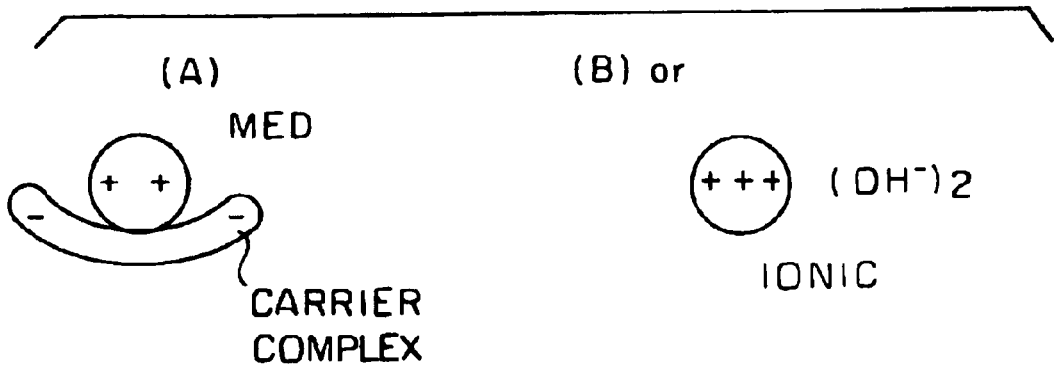
FIGS. 2a and 2b illustrate the electrostatic attraction of a bioactive ingredient for a carrier complex (2a) iron an ionic complex (2b).
Figure 3:
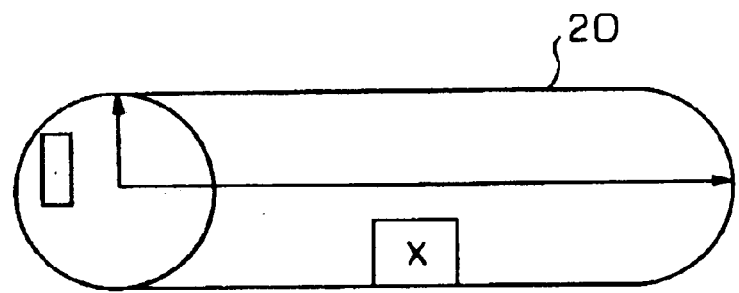
FIG. 3 illustrates an implantable device.

It is commonly observed that charged particles do not easily penetrate membranes, because, generally, charged particles are not lipid soluble. This is generally true, but is not universally true. If a particle is fairly small, the charge comparatively large, and the membrane relatively thin, an ion can be dragged through the lipid bi-layer membrane. By arranging the electrical vector in the same direction as the other diffusion vectors, this process can be improved by a factor of three, as shown in FIG. 2. This is particularly useful for certain ions delivered perpendicular to the membrane, such as the thin membranes of the nasal conchae in the nose.

If a charged complex is to be slid across a membrane, in a parallel direction, until the complex reaches neutrality, the anatomy can be used for delivery. By controlling the pH difference between the recipient and target compartments, one can determine the length of the electrical vector with good accuracy. There the complex becomes neutral, and it penetrates the membrane in the usual way.

As a non-limiting example, the largest and best known of the BCECs is that which exists between the mouth and the nose. This area is convenient and easy to test, and lends itself to experimentation. The mouth-nose circuit has a natural partition in the hard and soft palates, which can be easily modeled as an electrophoretic sheet. The fluids of the nasal cavity are continually oxidized by breathing, while the oral cavity is usually closed, except for speech or exhalation. The expression of carbon dioxide during speech or exhalation forms the basic bicarbonate ion $(HCO_3)$[13] in saliva. These natural processes maintain the two compartments in different states of oxidation, with the nose at a lower pH than the mouth. This gradient is maintained homeostatically, and results in a concentration cell.

This concentration cell can readily be observed using an oscilloscope or sensitive volt meter. Currents between these two compartments are generally approximately 80–100 milli-volts. These can be detected by touching a probe or a wick electrode to the mucosa of both compartments. These values can also be calculated from the pH ranges in the literature.

In order to deliver a bioactive material to an implanted device, the direction of the electrical vector can be reversed to oppose the others, and maintain a charged medication or complex in the location of the implanted device. Because the electrical vector has been reversed to oppose ordinary diffusion, delivery to an implanted device by this method keeps the bioactive material from leaving the site of the implanted device for the time the electrical vector is present. Afterward, the forces of diffusion reassert themselves, and medication diffuses normally from the implantable device.

A stent can be used as a nonlimiting example of an implanted device which can be charged or recharged by the method of the present invention. As shown in FIG. 2, the stent is in the form of a uniform cylindrical pipe 2 of length x and radius r. There is initially a constant flow of blood through the stent. Although blood and lymph are non-Newtonian fluids with changing viscosities, because of the alignment and change of shape of cells during flow, these cells actually behave in a Newtonian manner during flow, i.e., they have a constant viscosity.

The stent 20 shown in FIG. 2 illustrates an implanted device. In this case:

A=hydrated cross sectional area of a charged drug particle r=radius of the stent, a constant x=length of the stent, a constant N=viscosity of the fluid contained in the stent V=dx/dt=velocity of the fluid through the stent, a variable P=pressure, a variable W=work, a constant Sears and Zemansky, *University Physics* 10$^{th}$ Edition, Young and Freedman, editors, on page 447 has the formula for a velocity through a stent as illustrated above as:

$$V=\{(P_2-P_1)(r_{22}-r_{12})\}/4Nx$$

The integration of Newton's law of force and viscosity given in U.S. Pat. No. 6,414,033, gives:

$$r=Wt/NA$$

Differentiating r with respect to t gives:

$$Dr/dt=W/NA$$

Application of the chain rule gives the expression for dr/dx:

$$Dr/dx=[4WX]/A(P_2-P_1)(r22-r12)$$

The viscosity has been cancelled from the equation because the work term accounts for viscosity.

The electrostatic work on the particle is:

W=zFE where E is the EMF calculated by any conventional means, such as the Nernst or Boltzman equations.

Z=the valence of the ion, and F is the Faraday constant.

Thus the ion experiences continual force in the r direction and either continual or intermittent motion in the x direction, depending upon what assumption is made about the circulation. Accounting for the heartbeat of a relaxed patient, the blood remains stationary for from about 0.3 to about 0.5 seconds per beat. At 60 beats per minute, this is approximately 18 to 30 seconds added to the contact time in the stent, on a cumulative basis per minute. This can be added to the calculations of travel from any given position for an ion in the lumen of the stent.

Given the induced charge on the stent, it is now possible to calculate the time and force necessary to recharge it with an ionic medication using Stokes law:

F=force exerted on a spherical particle, and rp is the particle radius $F=6\pi Nr_p dr/dt$ for the r direction, and dx/dt for the x direction. In the r direction this force is also equal to the EMF applied, and limits the speed of travel according to the viscosity.

In general, for an implanted device, the length of the implanted device is about 1 to about 10 cm in length. The speed of the circulation is intermittent, allowing more time for exchange. The force of dissociation of a charged particle or ligand complex must be less than that of the EMF applied, so that the molecule of bioactive material leaves the complex for the implanted device. The complex must discharge its biomedical material along the time given by the above equations, that is, the time necessary for the particle to pass through the implanted device.

The system can be manipulated in a variety of ways:

1. controlling the induced charge on the implanted device
2. controlling the attractive force of the bioactive material molecule for its complex versus the EMF applied by the implanted device.
3. the length of the implanted device
4. controlling the local viscosity of the blood or lymph
5. artificially slowing the heartbeat to achieve a longer contact between the fluids containing the bioactive material and the implanted device.

As long as the implantable device can be charged according to the present invention, it can be made of any physiologically compatible material that can be used to hold another to release a bioactive material. Examples of such materials include stainless steel, tantalum, titanium , nitinol, gold, platinum, inconel, iridium, silver, tungsten, or alloys of these with each other or any other biocompatible metal; carbon, carbon fibers, cellulose acetate, cellulose nitrate, silicone, polyethylene terephthalate, polyurethane polyamide, polyester, polyorthoesters, polyanhydrides, polyether sulfones, polycarbonates, polypropylene, high molecular weight polyethylene, polytetrafluoroethylene, or other biocompatible polymer or mixtures of copolymers thereof; biodegradable materials such as polylactic acid, polyglycolic acid or mixture of copolymers thereof; proteins, extracellular matrix components; collagen, fibrin or other biologic agent; or a suitable mixture of any of these.

To move a positively charged (i.e., acid) bioactive material to the implanted device, the implanted device must be negatively charged with respect to the bioactive material. Conversely, to move a negatively charged (i.e., basic) bioactive material to the implanted device, the implanted device must be positively charged with respect to the bioactive material.

Alternatively, the bioactive material may be in the form of a neutral complex of the bioactive material and a suitable carrier molecule, such that the Kd of the carrier is less than the electrostatic force of attraction exerted by the implanted device for the bioactive agent. Amino acids and their congeners are ideal carriers, although, given the requirement that the Kd of the carrier be less than the electrostatic force of attraction exerted by the implanted device for the bioactive material, one skilled in the art can readily design an appropriate carrier for the bioactive material.

Examples of bioactive agents that can be delivered to an implanted device by the method of the present invention include antiplatelets, anticoagulants, antifibrins, antithrombins, and antiproliferatives. Other bioactive agents which can be used in the present invention include cytostatic agents, angiotensin converting agents, calcium channel blockers, prostaglandin inhibitors, monoclonal antibodies, phosphodiesterase inhibitors, serotonin blockers, steroids, thioprotease inhibitors, PDGF antagonists, and nitric oxide. Other bioactive materials include alpha-interferon and genetically engineered epithelial cells.

For example, to charge a stent implanted in a blood vessel, an antiproliferative agent such as methotrexate is delivered to the stent to inhibit over-proliferation of smooth muscle cells and thus inhibit restenosis of the dilated segment of the blood vessel. Additionally, localized delivery of an antiproliferative agent is also useful for treating a variety of malignant conditions characterized by rapid vascular growth. In such cases, the implantable device can be placed in the arterial supply of the tumor to provide a means for delivering a relatively high dose of the antiproliferative agent directly to the tumor.

A variety of other bioactive materials are suitable for use when the implantable device is configured as something other than a coronary stent. For example, an anti-cancer chemotherapeutic agent can be delivered by the device to a localized tumor. More particularly, the implantable device can be placed into an artery supplying blood to the tumor or elsewhere to deliver a relatively high and prolonged dose of the agent directly to the tumor, while limiting systemic exposure and toxicity. The agent may be a curative, a pre-operative debulker for reducing the size of the tumor, or a palliative which eases the symptoms of the disease. It should be noted that the bioactive material in the present invention is delivered directly from the implanted device, and not by passage from an outside source through any lumen defined in the device. The bioactive material of the present invention may, of course, be released from the device into any lumen defined in it, and that lumen may carry some other agent to be delivered through it.

Dopamine, or a dopamine agonists such as bromocriptine mesylate or pergolide mesylate is useful in treating neurological disorders such as Parkinson's disease. The device could be placed into the vascular supply of the thalamic substantia nigra for this purpose, or elsewhere, localizing treatment in the thalamus.

A wide range of other bioactive materials can be delivered to the implanted device for treatment of a variety of conditions. Nonlimiting examples of such bioactive materials include paclitaxel, estrogen or estrogen derivatives, heparin or another thrombin inhibitor; antithrombogenic agent such as hirudin, hiruolog, argatoban, D-phenylalanyl-L-poly-L-arginiyl chloromethyl ketone, or mixtures thereof; urokinase, streptokinase, tissue plasminogen activator, or other thrombolytic agent or mixtures thereof; a fibrinolytic agent; a vasospasm inhibitor; a calcium channel blocker; a nitrate, nitric oxide, a nitric oxide promoter or other vasodilator; an antimicrobial agent or antibiotic; aspirin, ticlopidine or other antiplatelet agent; antimitotics such as colchicines or another microtubule inhibitor; cytochalasin or other actin inhibitor; a remodeling inhibitor; cytochalasin or other actin inhibitor; deoxyribonucleic acid, an antisense nucleotide or another agent for molecular genetic intervention; GP IIa/IIIa, GP Ib-IX or another inhibitor of surface glycoprotein receptor; methotrexate or another antimetabolite or antiproliferative agent; anti-cancer chemotherapeutic agents; anti-inflammatory steroids; immunosuppressive agents; antibiotics; dopamine or bromocriptine mesylate, pergolide mesylate or other dopamine agonist; $^{6O}Co$, $^{192}Ir$, $^{32}p$, $^{111}In$, $^{90}y$, $^{99}Tc$, or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix composition, a cellular component or another biological agent; captopril or other angiotensin converting enzyme inhibitor; ascorbic acid, alphatocopherol, superoxide dismutase, or other free radical scavenger, iron chelator or antioxide; angiopeptin; radiolabelled elements or compounds; or mixtures of any of these.

Disease states in which one would deliver bioactive materials involving "angiogenic activity" include, but are not limited to, myocardial conditions, trauma, tumors (benign and malignant) and tumor metastases, ischemia, tissue and graft transplantation, diabetic microangiopathy, neovascularization of adipose tissue and fat metabolism, revascularization of necrotic tissue, eye conditions (e.g., retinal neovascularization), growth of new hair, and ovarian follicle maturation.

While the foregoing types of bioactive materials have been used to treat or prevent restenosis and other conditions, they are provided by way of example and are not meant to be limiting, since other bioactive agents can be introduced in the same manner. Treatment of diseases using the above bioactive materials are known in the art. Furthermore, the calculation of dosages, dosage rates, and appropriate duration of treatment are well known in the art.

The implanted medical device can be designed for continuous administration of a bioactive material. In this case, the bioactive material can be periodically administered to the patient either by intravenous or transmembrane techniques. The amount of bioactive material to be administered each time depends on the rate of absorption of the material from the stent into the blood, which can be either higher or lower than the conventional therapeutic dosage, since the bioactive material is administered directly to the site of release rather than through the digestive system, etc.

The present invention provides a non-invasive method for charging an implanted device with a bioactive material, or for re-charging an implanted device with a bioactive material.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A method for charging or re-charging an implanted device with a bioactive material comprising:
   a. introducing a charge into the implanted device;
   b. introducing a bioactive material in ionic form or in a neutral complex that will dissociate tonically in the presence of the charge on the implanted device.

2. The method according to claim 1 wherein the implanted device is a stent.

3. The method according to claim 2 wherein the bioactive material is a material for treating or preventing restenosis.

4. The method according to claim 1 wherein the bioactive material is introduced intravenously or trans-membrane.

5. The method according to claim 1 wherein the bioactive material is in the form of a neutral complex of the bioactive material and a carrier molecule for the bioactive ingredient.

6. The method according to claim 5 wherein the carrier is an amino acid or a congener thereof.

7. The method according to claim 5 wherein the carrier is a molecule such that the KD of the carrier is less than the electrostatic force of attraction exerted by the bioactive material.

8. The method according to claim 1 wherein the bioactive material is in the form of a stable charged complex with a direct attraction for the charge in the implanted device.

9. The method according to claim 1 wherein the bioactive material is selected from the group consisting of an antiproliferative agent, an anti-cancer therapeutic, dopamine, a dopamine agonist, a thrombin inhibitor, an estrogen, an androgen, an antithrombogenic agent, a clot dissolver, a fibrinolytic agent, a vasospasm inhibitor, a calcium channel blocker, a vasodilator, an antimicrobial agent, an antibiotic, an antiplatelet agent, an antimitotic, an actin inhibitor, a remodeling inhibitor, a deoxynucleic acid, an antisense nucleotide, an inhibitor of surface glycoprotein receptor, a steroid, an immunosuppressive agent, a radiotherapeutic compound, a radiopaque agent, a peptide, a protein, an enzyme, an extracellular matrix composition, an angiotensin converting enzyme inhibitor, a free radical scavenger, and mixtures thereof.

10. An implantable device which is capable of being charged or re-charged without removal from the body in which it is implanted comprising a device made of material which can be induced to form a charge and to retain the charge sufficiently long to act electrostatically and attract a charged substance to itself.

11. The device according to claim 10 which is in the form of a stent.

12. The device according to claim 11 wherein the bioactive material is a material for treating or preventing restenosis.

13. The device according to claim 10 which is made of a biocompatible material selected from the group consisting of plastic having metal atoms covalently bonded thereto, ceramic having metal atoms covalently bonded thereto, ceramic having an electronic transfer system, and porous metals in which a bioactive material is embedded therein.

14. The device according to claim 10 wherein a metallic or capacitive strip is embedded within the device.

\* \* \* \* \*

UNITED STATES PATENT AND TRADEMARK OFFICE
CERTIFICATE OF CORRECTION

PATENT NO. : 6,699,282 B1
DATED : March 2, 2004
INVENTOR(S) : Nicolas Sceusa

It is certified that error appears in the above-identified patent and that said Letters Patent is hereby corrected as shown below:

Column 2,
Line 44, delete "tonically" and insert therefor -- ionically --.

Column 4,
Line 29, delete "chare" and insert therefor -- charge --.

Column 9,
Line 44, delete "tonically" and insert therefor -- ionically --.

Signed and Sealed this

Twenty-ninth Day of June, 2004

JON W. DUDAS
*Acting Director of the United States Patent and Trademark Office*